(12) United States Patent
Biedermann et al.

(10) Patent No.: US 11,813,002 B2
(45) Date of Patent: Nov. 14, 2023

(54) DEVICE FOR PLACING A RECEIVING PART ONTO A HEAD OF A BONE ANCHORING ELEMENT

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE); Dimosthenis Dandanopoulos, VS-Schwenningen (DE); Timo Biedermann, Trossingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/143,606

(22) Filed: Jan. 7, 2021

(65) Prior Publication Data
US 2021/0186577 A1 Jun. 24, 2021

Related U.S. Application Data (63) Continuation of application No. 16/289,331, filed on Feb. 28, 2019, now Pat. No. 10,912,593, which is a
(Continued)

(30) Foreign Application Priority Data
Mar. 14, 2014 (DE) .................................. 14160126.0

(51) Int. Cl.
*A61B 17/70* (2006.01)
(52) U.S. Cl.
CPC ...... *A61B 17/7082* (2013.01); *A61B 17/7076* (2013.01)

(58) Field of Classification Search
CPC ........ A61B 17/70–7056; A61B 17/7076–7092
See application file for complete search history.

(56) References Cited

U.S. PATENT DOCUMENTS

| 5,672,176 A * | 9/1997 | Biedermann ...... A61B 17/7032 606/65 |
|---|---|---|
| 6,440,133 B1 | 8/2002 | Beale et al. |

(Continued)

FOREIGN PATENT DOCUMENTS

| CN | 102149344 A | 8/2011 |
|---|---|---|
| EP | 1 105 057 | 2/2001 |

(Continued)

OTHER PUBLICATIONS

Extended European Search Report for Application No. 14160126.0, dated Jan. 5, 2015 (12 pages).
(Continued)

*Primary Examiner* — Eduardo C Robert
*Assistant Examiner* — Steven J Cotroneo
(74) *Attorney, Agent, or Firm* — Lewis Roca Rothgerber Christie LLP (57) ABSTRACT

A device for placing a receiving part of a bone anchoring device onto a head of a bone anchoring element includes a holding portion, a collet configured to be held by the holding portion, the collet having a tubular body extending along a longitudinal axis, and a distal end portion configured to be flexibly expanded and compressed in a radial direction, and a plunger configured to be positioned in the collet. The collet is movable axially relative to the plunger between a first position wherein the distal end portion of the collet is configured to have a first width in a first radial direction and the plunger prevents the distal end portion from assuming a width less than the first width, and a second position wherein
(Continued)

the distal end portion of the collet is radially compressible to a second width that is less than the first width.

20 Claims, 8 Drawing Sheets

Related U.S. Application Data continuation of application No. 14/645,319, filed on Mar. 11, 2015, now Pat. No. 10,258,390.

(60) Provisional application No. 61/953,510, filed on Mar. 14, 2014.

(56) References Cited

U.S. PATENT DOCUMENTS

| | | | | |
|---|---|---|---|---|
| 6,471,705 | B1* | 10/2002 | Biedermann | A61B 17/7037 |
| | | | | 606/271 |
| 8,328,817 | B2 | 12/2012 | Strauss | |
| 8,852,239 | B2* | 10/2014 | Jackson | A61B 17/7037 |
| | | | | 606/267 |
| 9,308,027 | B2* | 4/2016 | Jackson | A61B 17/7035 |
| 9,480,517 | B2* | 11/2016 | Jackson | A61B 17/7008 |
| 2003/0023243 | A1* | 1/2003 | Biedermann | A61B 17/7037 |
| | | | | 606/308 |
| 2003/0125741 | A1* | 7/2003 | Biedermann | A61B 17/7035 |
| | | | | 606/264 |
| 2004/0225289 | A1* | 11/2004 | Biedermann | A61B 17/8605 |
| | | | | 606/279 |
| 2007/0043378 | A1 | 2/2007 | Kumar et al. | |
| 2007/0161998 | A1* | 7/2007 | Whipple | A61B 17/7032 |
| | | | | 606/86 A |
| 2007/0162009 | A1* | 7/2007 | Chao | A61B 17/708 |
| | | | | 606/86 A |
| 2008/0200918 | A1 | 8/2008 | Spitler et al. | |
| 2009/0105712 | A1* | 4/2009 | Dauster | A61B 17/7086 |
| | | | | 606/99 |
| 2009/0163963 | A1* | 6/2009 | Berrevoets | A61B 17/8875 |
| | | | | 606/104 |
| 2009/0264896 | A1* | 10/2009 | Biedermann | A61B 17/7076 |
| | | | | 606/104 |
| 2010/0114108 | A1 | 5/2010 | Strauss | |
| 2011/0046683 | A1* | 2/2011 | Biedermann | A61B 17/7082 |
| | | | | 606/305 |
| 2011/0152949 | A1* | 6/2011 | Biedermann | A61B 17/7037 |
| | | | | 606/305 |
| 2011/0166606 | A1* | 7/2011 | Stihl | A61B 17/7086 |
| | | | | 606/279 |
| 2011/0263945 | A1* | 10/2011 | Peterson | A61B 17/025 |
| | | | | 606/300 |
| 2011/0282402 | A1 | 11/2011 | Chao et al. | |
| 2012/0068413 | A1 | 3/2012 | Putt et al. | |
| 2012/0239092 | A1 | 9/2012 | Jones et al. | |
| 2012/0253402 | A1 | 10/2012 | McLean | |
| 2012/0296171 | A1 | 11/2012 | Lovell et al. | |
| 2013/0018428 | A1* | 1/2013 | Harper | A61B 17/8685 |
| | | | | 606/305 |
| 2013/0023941 | A1 | 1/2013 | Jackson et al. | |
| 2013/0060293 | A1* | 3/2013 | Jackson | A61B 17/7037 |
| | | | | 606/305 |
| 2013/0144346 | A1 | 6/2013 | Jackson et al. | |
| 2014/0142634 | A1* | 5/2014 | Schlaepfer | A61B 17/7037 |
| | | | | 29/428 |
| 2014/0188175 | A1* | 7/2014 | Mishra | A61B 17/7037 |
| | | | | 606/279 |

FOREIGN PATENT DOCUMENTS

| | | |
|---|---|---|
| JP | 2013-540453 A | 11/2013 |
| WO | WO 2011/159492 A1 | 12/2011 |
| WO | WO 2013/187928 A1 | 12/2013 |

OTHER PUBLICATIONS

European Search Report; Application Serial No. 14160126.0; dated Aug. 1, 2014; Completion Date Jul. 25, 2014; 5 Sheets.

* cited by examiner

DEVICE FOR PLACING A RECEIVING PART ONTO A HEAD OF A BONE ANCHORING ELEMENT

CROSS-REFERENCE TO RELATED APPLICATIONS

This application is a continuation of U.S. patent Ser. No. 16/289,331, filed Feb. 28, 2019, which is a continuation of U.S. patent application Ser. No. 14/645,319, filed Mar. 11, 2015, now U.S. Pat. No. 10,258,390, which claims the benefit of U.S. Provisional Patent Application Ser. No. 61/953,510, filed on Mar. 14, 2014, the contents of which are hereby incorporated by reference in their entirety, and claims priority to European Patent Application EP 14160126.0, filed on Mar. 14, 2014, the contents of which are hereby incorporated by reference in their entirety.

BACKGROUND

Field of the Invention

The present invention relates to a device or tool for placing a receiving part of a bone anchoring device onto a head of a bone anchoring element. The present invention further relates to such a receiving part of a bone anchoring device. The device or tool includes a holding portion, a collet for engaging the receiving part, and a corresponding engagement feature.

Fractures of the spinal column, arthrodesis, scoliosis, etc. are often treated by stabilizing the spinal column using bone anchors applied to two or more vertebrae and connecting the same via rigid or dynamically flexible stabilization rods, such as to define a predetermined relative position and movement tolerance for each of the vertebrae involved. In operation, vertebrae are first selectively supplied with bone anchors and a stabilization rod is then attached to connect each of the bone anchors. The connection of each of the bone anchors is established by a receiving part, which connects to a head of the bone anchoring element and receives a spinal rod in a rod receiving channel thereof.

In recent years, there has been a tendency to assemble such bone anchoring devices in situ. Methods of in situ assembling of the bone anchoring devices advantageously allow for easier or better visual inspection of several structures in place, such as particular neurological structures, etc., which may be critical or important for certain procedures, since the receiving parts are attached to the bone anchors in a subsequent step. New clinical methods and surgical steps may also become possible and/or easier to perform. Moreover, particular advantages arise in that preparation of very small MIS (minimally invasive surgery) accesses is made possible.

For example, a bone anchoring element is anchored in a vertebra first, where after a receiving part is placed onto a head of the bone anchoring element. However, such construction necessitates that the receiving part allows the head to be loaded therein from a bottom side of the receiving part. As a consequence, a bottom opening of the receiving part has an increased diameter, and the head has to be received by a portion of a pressure element or an inner cap provided within the receiving part which encompasses the head and locks the head against a seat formed adjacent the bottom opening. One early example is described in U.S. Pat. No. 6,471,705 B1 and EP 1 105 057 A1.

In view of the above, a need has arisen to also provide a device or tool that is suitable for placing a receiving part onto a head of a bone anchoring element.

Description of Related Art

U.S. 2011/0166606 A1 discloses a reduction tool designed to engage a body portion having a rod receiving channel and to insert a spinal rod therein. The tool includes an outer tube having engagement features at the distal end thereof, two opposite slots through which the rod is inserted, and an inner tube which advances a locking cap and the rod. The proximal end of the outer tube also has two opposite slots such that a pivot point is formed in a middle portion thereof and compression of the proximal end of the outer tube results in expansion of the distal end. As a consequence of such manipulation, engagement of a receiving part by the protruding engagement features provided at the distal end of the outer tube can be facilitated. Upon engagement, those protrusions are led into corresponding recesses formed in an outer circumferential surface of the receiving part.

However, the above described reduction tool is configured to engage a receiving part in a state in which the receiving part is preassembled with the bone anchoring element, and further, due to the pivoting expansion to engage and disengage the receiving part at its circumferential surface, a relatively large space is need in a patient's body rendering the tool less suitable for minimal invasive surgery and in situ operation.

U.S. 2012/0296171 A1 discloses an inserter including a driver and a receiver member wherein a head of a bone anchor to be inserted is securely connected to the inserter by virtue of the receiver member which is used in a collet-like fashion. The receiver member thereby receives the head and a cylindrical body is slid over a conical portion of the receiver member to compress deflectable flanges onto the head. A driving operation may then be performed with regard to the bone anchor. In this device, however, the receiver member is part of the inserter and cannot be released and used to receive a rod.

SUMMARY

It is thus an object of the invention to provide a device or tool for placing a receiving part onto a head of a bone anchoring element which improves known methods and devices.

According to embodiments of the invention, the device includes a holding device and a collet held by the holding device. The collet has a distal end portion which is configured to be flexibly expanded and/or compressed, which allows engaging and/or disengaging of a corresponding receiving part. An engagement feature is provided at an outer contour, or outer surface, of the distal end portion of the collet. The engagement feature may engage a portion of an inner wall of a rod receiving channel or a bore of a receiving part.

More specifically, the engagement feature is not provided at an inner surface of a tube or shaft as proposed in some prior art, but instead on an outer surface, to engage an inner wall of the receiving part. The inner wall may be that of an inner bore extending, for example, from a top end to a bottom end of the receiving part or may be that of a rod receiving channel which is typically formed extending from the top end of the receiving part. Engagement with other inner walls is possible as well, as long as the engagement takes place within a perimeter of the receiving part and the release operation does not occur in a space beyond such perimeter, in particular by expansion. In embodiments described herein, the device may be compressed at its distal end when releasing the receiving part, for example, after implantation.

Consequently, it is not necessary to engage the receiving part on any of its circumferential outer surfaces. This, in turn, allows narrower channels through the tissue of the human body to be used to approach a target bone. Hence, aspects and embodiments of the invention are particularly applicable in minimally invasive surgery (MIS) and in situ assembly.

Engagement and disengagement of the device or tool from the receiving part is facilitated by radial expansion and compression of the distal end portion of the collet, respectively. It is not necessary to use an inner thread, which is generally available at inner walls of receiving parts to facilitate locking of a rod by a locking screw, to engage the device. Instead, quick locking and releasing of the receiving part with improved tactile response is possible when placing the receiving part onto the head.

With regard to the receiving part described herein, only minor structural changes have to be applied, if any, to generally available receiving parts. For example, engagement features may be provided at the inner walls of the rod receiving channels. The engagement features may be protrusions, spring-like projections, noses, recesses, and/or similar features which allow a latching connection with corresponding features of the device or tool. Such engagement features may even be provided within a region of an inner thread—if present. According to specific embodiments, even an inner thread might be considered to provide corresponding latching features into which the engagement features of the device or tool is configured to expand during engagement.

In one embodiment, a device or tool is provided for application to a bone anchoring device, wherein an inner cap is provided within a receiving part of the bone anchoring device, where the inner cap clamps the head of the bone anchoring element, thereby allowing frictionally limited movement of the clamped bone anchoring element when the device has not yet been finally locked. In this situation, the device or tool allows for a more efficient method for placing the receiving part onto the head.

BRIEF DESCRIPTIONS OF THE DRAWINGS

Advantageous features and aspects of the present invention will become more apparent from a detailed description of specific embodiments taken in conjunction with the accompanying drawings, wherein.

DETAILED DESCRIPTION

An embodiment of a device or tool for assembling a bone anchoring device is described with respect to FIGS. 1-9, a corresponding embodiment of a receiving part and an inner cap of a bone anchoring device is described with reference to FIGS. 10A-11B, and an illustrative example of a method of using the device or tool with the bone anchoring device is described with reference to FIGS. 12-16C.

Figures 1, 2:
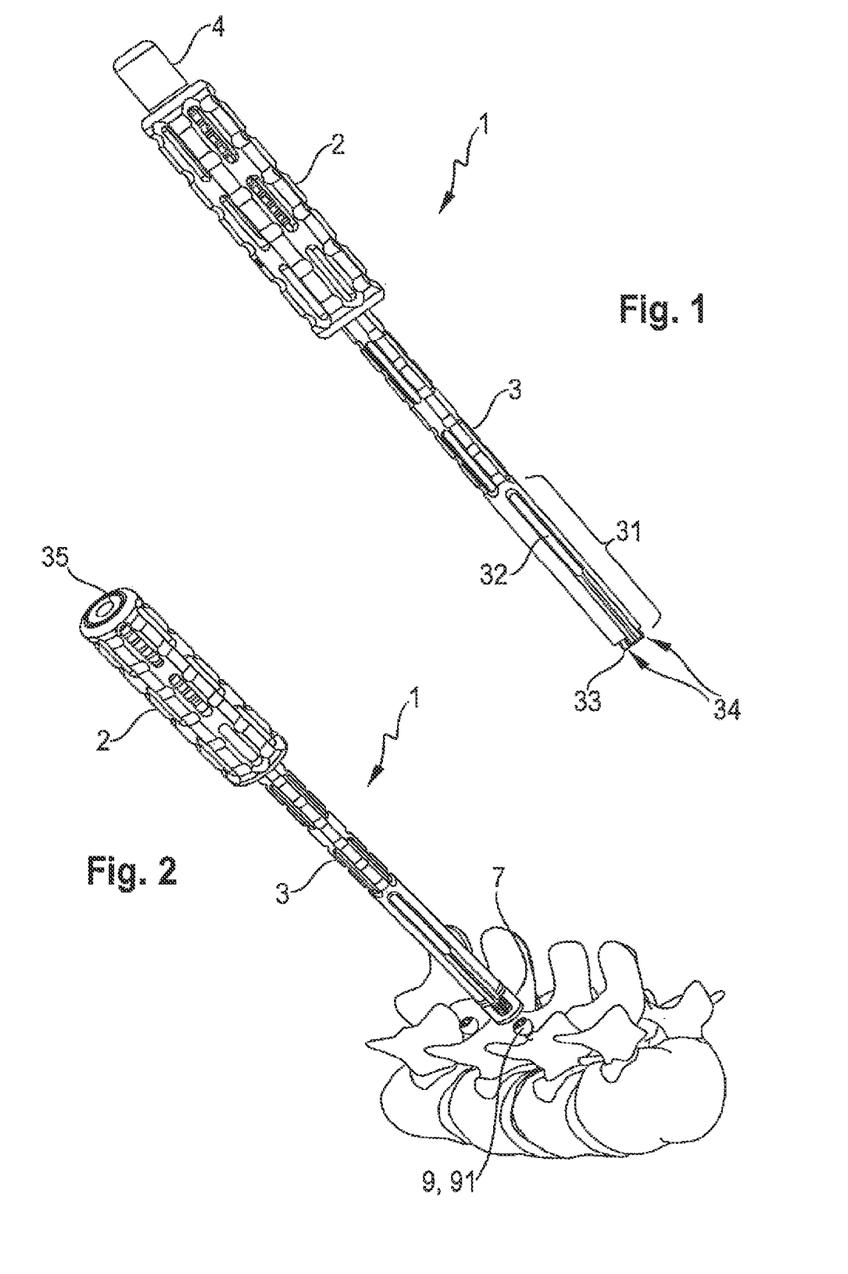
FIG. 1 shows a perspective view of the device or tool according to an embodiment of the invention with a collet in a locked position.
FIG. 2 shows the device shown in FIG. 1 in use just prior to placement of a receiving part onto a head of a bone anchoring device and with an operation portion of the device having been removed.
Figures 3, 4A, 4B, 4C:
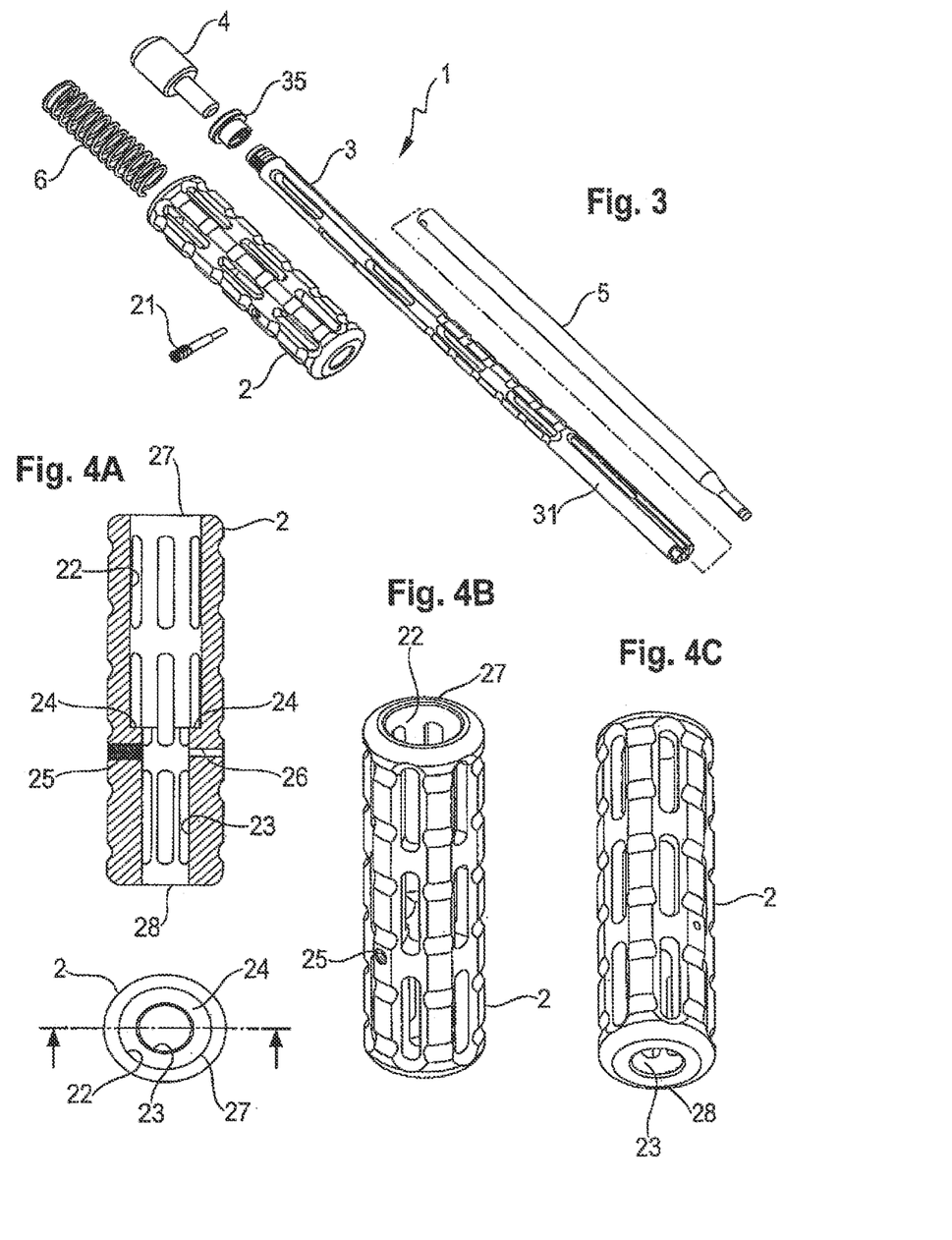
FIG. 3 shows the device shown in FIG. 1 in a disassembled state.
FIG. 4A shows top and cross-sectional views of the holding portion of the device shown in FIGS. 1 to 3.
FIG. 4B shows a top perspective view of the holding portion shown in FIGS. 4A and 4B.
FIG. 4C shows a bottom perspective view of the holding portion shown in FIGS. 4A to 4C.

An overview of the device 1 for placing a receiving part onto a head of a bone anchoring element is shown in FIGS. 1-3. The device 1 according to this embodiment includes a holding portion 2, a collet 3, an operation portion 4, a plunger 5, and a resilient member 6 (e.g., a spring). A fixation device 21 provided as a follower pin can be applied to the holding portion 2 to establish a connection with plunger 5, and a cap-like proximal end portion 35 can be provided to the collet 3 to allow attaching the operation portion 4 to a proximal end of the collet 3 and to provide a proximal abutment face 353 for the resilient member 6 as will be further described below.

FIG. 1 shows the device 1 in a state in which the operation portion 4 is not pressed, and as a consequence, the collet 3, or a distal end portion 31 thereof, is in a locked state since a tip portion 52 of plunger 5 extends into the distal end portion 31 of the collet 3, as will be explained in further detail below.

Figure 14:
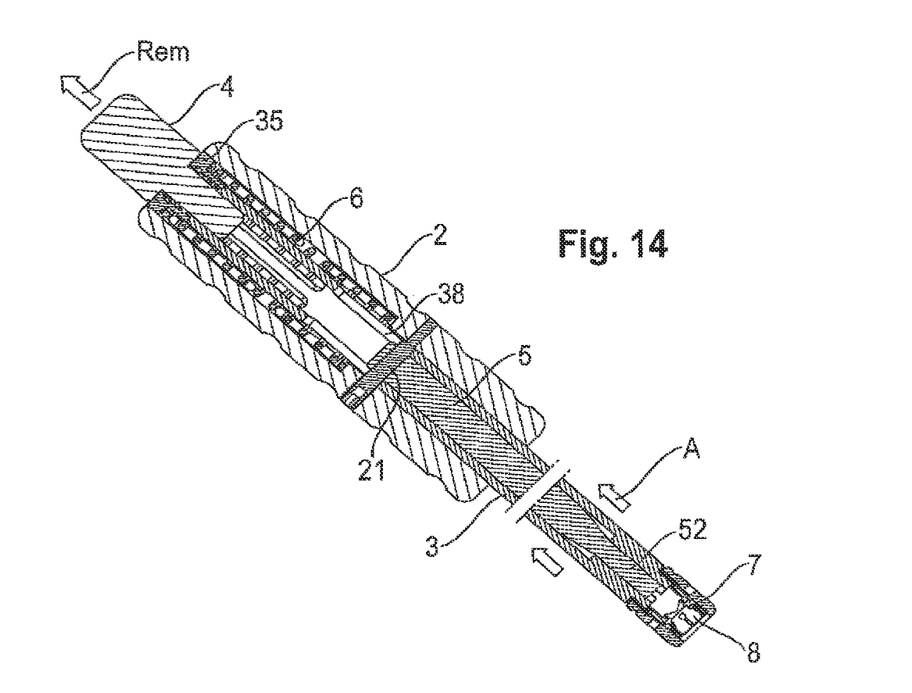
FIG. 14 shows a cross-sectional view of the device in the same state as shown in FIG. 13C, with the distal end portion of the collet being locked by a plunger of the device or tool.

Similarly, the device 1 as shown during use in FIG. 2 is also in the locked state, however, the operation portion 4 has been removed from the device 1. In the locked state, a receiving part 7 is securely attached to (e.g., connected to) the distal end portion 31 of the collet 3, and may thus be safely guided through an incision channel cut into tissue of a patient (not shown) towards a head 91 of a bone anchoring element 9, which has already been anchored in a pedicle of a vertebra as shown in FIG. 2. The state shown in FIG. 2 substantially corresponds to that shown in FIG. 14 illustrating a method of use, which will be discussed in further detail below.

FIGS. 4A to 9 illustrate the separate parts of the device or tool 1.

The holding portion 2 is shown in FIGS. 4A-4C in top, cross-sectional, top perspective, and bottom perspective views, respectively. The holding portion 2 of this embodiment has a substantially tubular shape with a textured profile at its outer surface to allow safe gripping by operating staff. In use, the holding portion 2 is held with one hand, and a thumb may for example be used to press the operation portion 4. The holding portion 2 has an inner bore extending from a proximal end 27 towards a distal end 28 thereof. A first bore portion 22 having a comparatively large diameter extends from the proximal end 27, and a second bore portion 23 extends from the distal end 28 towards one another. The second bore portion 23 has a smaller diameter as compared with the first bore portion 22. At the transition between the first bore portion 22 and the second bore portion 23, which both extend along a common longitudinal axis, a shoulder 24 serving as a distal abutment face for one end of the resilient member 6 further described below is formed.

A threaded bore 25 transversely extends through a wall of the holding portion 2, and a further bore 26 having a smaller diameter extends through the wall of the holding portion 2 on an opposite side of the holding portion 2 along the same axis as threaded bore 25. Bores 25, 26 are configured to receive the fixation device 21 shown in FIG. 8. More specifically, the fixation device 21 has a threaded section 211 configured to be threaded into the threaded bore 25, a narrower unthreaded pin portion 213 configured to fit into the bore 26 of the holding portion 2, and a cylindrical middle portion 212 configured to slidably fit through an oblong aperture or hole 38 of the collet 3 further described below. The fixation device 21 functions as a follower pin and fixes the plunger 5 to the holding portion 2, such that both the holding portion 2 and the plunger 5 together form a first unit of the device 1.

Figure 5A:
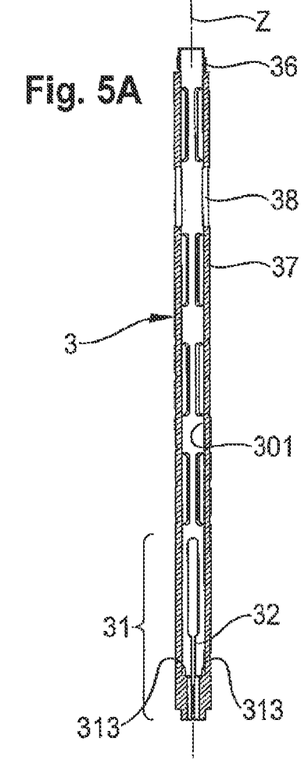
FIG. 5A shows a cross-sectional view of a tubular portion of a collet of the device shown in FIGS. 1 to 3.
Figure 5B:
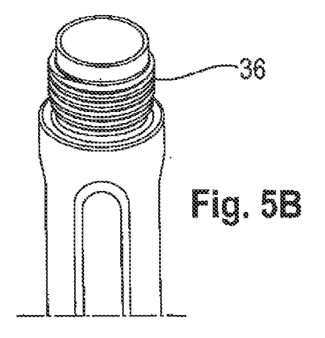
FIG. 5B shows an enlarged view of a proximal end of the tube of the collet shown in FIG. 5A.
Figure 5C:
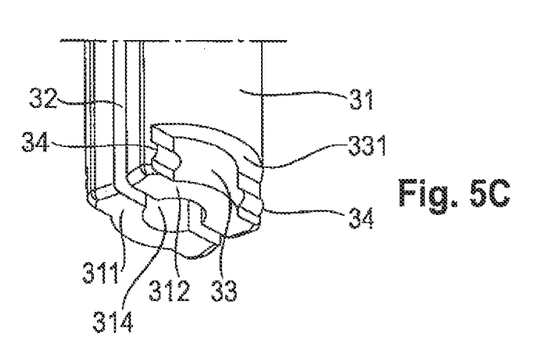
FIG. 5C shows an enlarged view of a distal end portion of the collet shown in FIG. 5A.
Figures 6A, 6B, 6C:
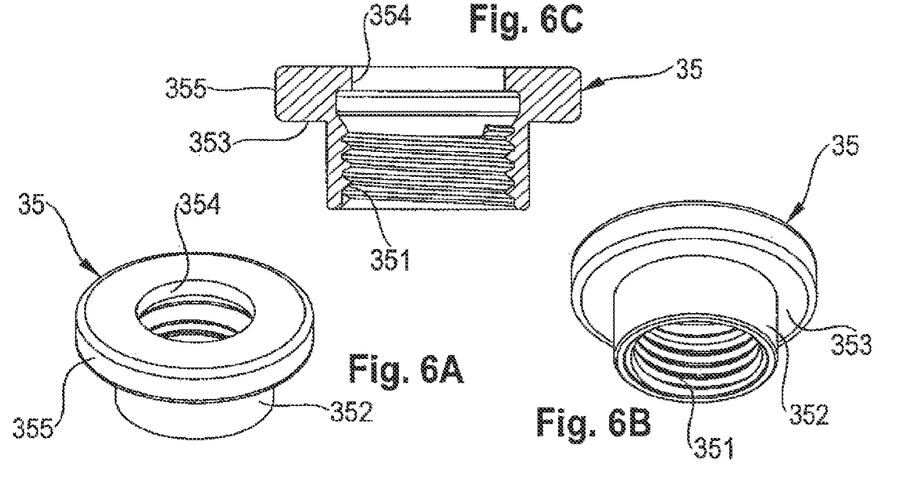
FIG. 6A shows a top perspective view of a separate proximal end portion of the collet according to the embodiment shown in FIGS. 1 to 3.
FIG. 6B shows a bottom perspective view of the proximal end portion of the collet shown in FIG. 6A.
FIG. 6C shows a cross-sectional view of the proximal end portion of the collet shown in FIGS. 6A and 6B.

The collet 3 is depicted in FIGS. 5A to 5C, and can include a separate proximal end portion 35 formed as a cap-like member as depicted in FIGS. 6A-6C. The collet 3 has a substantially tubular shape (tube 37) and its outer diameter is selected such as to slidably fit into the narrower second bore portion 23 of the holding portion 2. When assembled, a longitudinal axis Z of the collet 3 is coaxial with central axes of the first and second bore portions 22, 23 of the holding portion 2.

The collet 3 has a distal end portion 31 which is defined by two tongues 311, 312 which, in turn, are formed by two opposite slots 32 extending from a tip portion 33 of the collet 3 along the longitudinal axis Z up to a predetermined distance from the tip portion 33. The tip portion 33 of the distal end portion 31 is recessed from the overall cylindrical shape of the collet 3 and shaped such as to fit into a rod receiving channel and an inner bore of the receiving part 7. Upon engagement of the receiving part 7 by the distal end portion 31, an abutment face 331 of the collet 3 abuts a top face of the receiving part 7. Moreover, two rounded projections are formed as engagement features 34 on each of the tongues 311, 312 at the tip portion 33 of the collet 3. These projections extend in a lateral or radial direction from the collet 3.

The length of the slots 32 and the thickness of the walls of the collet 3 are dimensioned and the material or materials are selected such that both tongues 311, 312 are provided with resiliency such as to be expanded or compressed, depending on forces exerted during operation of the device 1.

Figure 7A:
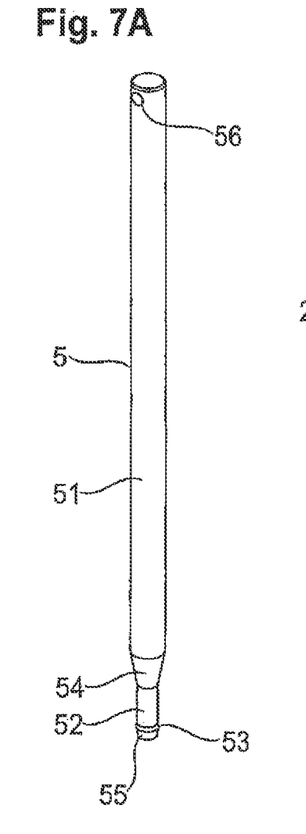
FIG. 7A shows a perspective view of a plunger of the device shown in FIGS. 1 to 3.
Figure 7B:
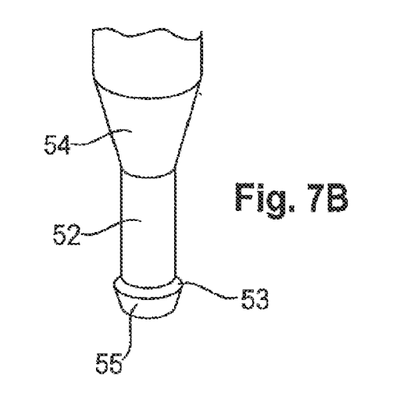
FIG. 7B shows an enlarged view of a tip portion of the plunger shown in FIG. 7A.
Figure 8:
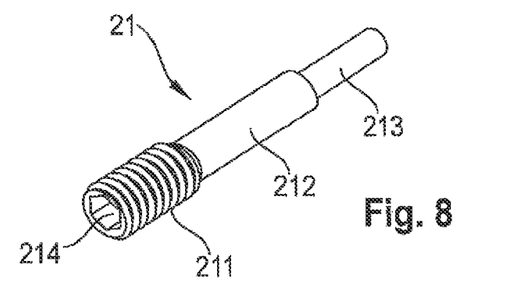
FIG. 8 shows a fixation device formed as a follower pin of the device shown in FIGS. 1 to 3.
Figure 9:
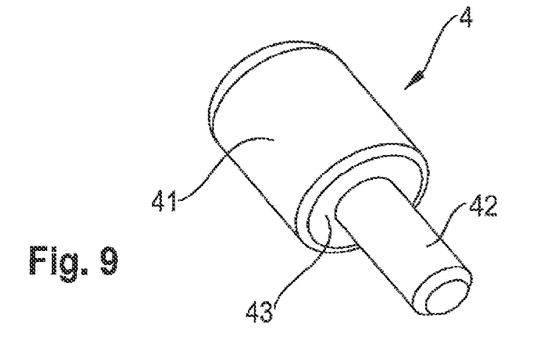
FIG. 9 shows an operation portion of the device shown in FIGS. 1 to 3.

For example, in this embodiment, the plunger 5 as shown in FIGS. 7A and 7B is used to prevent compression of, and may even expand, the tongues 311 and 312 of the collet 3. The plunger 5 is substantially rod-shaped and has a cylindrical portion 51 having a diameter configured to slidably fit into an inner bore 301 of the collet 3. The plunger 5 further has a partially cylindrical tip portion 52 having a smaller diameter as compared with the cylindrical portion 51 and a conical portion 54 at a transition between the cylindrical portion 51 and the tip portion 52. The diameter of the cylindrical part of the tip portion 52 of the plunger 5 is substantially the same as a diameter of a narrow diameter bore 314 (e.g., a bore hole) which is provided at a distal region of the collet 3 and extends from a shoulder 313 forming an end of the inner bore 301 of the collet 3 to a distal end of the tip portion 33.

In this specific embodiment, the tip portion 52 further includes a conical tip portion 55 having a slightly increasing diameter that is larger than that of the cylindrical part of the tip portion 52, and a conical transition portion 53 between the conical tip portion 55 and the cylindrical part of the tip portion 52. In addition, the plunger 5 has at its opposite end a bore 56 through which the fixation device 21 may be inserted, as described above, to form a first unit of the device 1 between the holding portion 2 and the plunger 5.

Since the plunger 5 is configured to slide within the inner bore 301 of the collet 3, the tip portion 52 of the plunger 5 is allowed to enter the narrow diameter bore 314 of the collet 3 wherein by virtue of the conical tip portion 55 having a larger diameter than the narrow diameter bore 314, the tongues 311, 312 are radially expanded (e.g., are spread apart or urged radially outwardly) in this embodiment. The length of the tip portion 52 including the conical tip portion 55 substantially corresponds to the length of the narrow diameter bore 314. From the above, it becomes clear that once the tip portion 52 has entered the bore 314 of the collet 3, compression of the tongues 311, 312 is impeded, and even a slight expansion (e.g., spreading) of the tongues 311, 312 may be facilitated.

Figure 12:
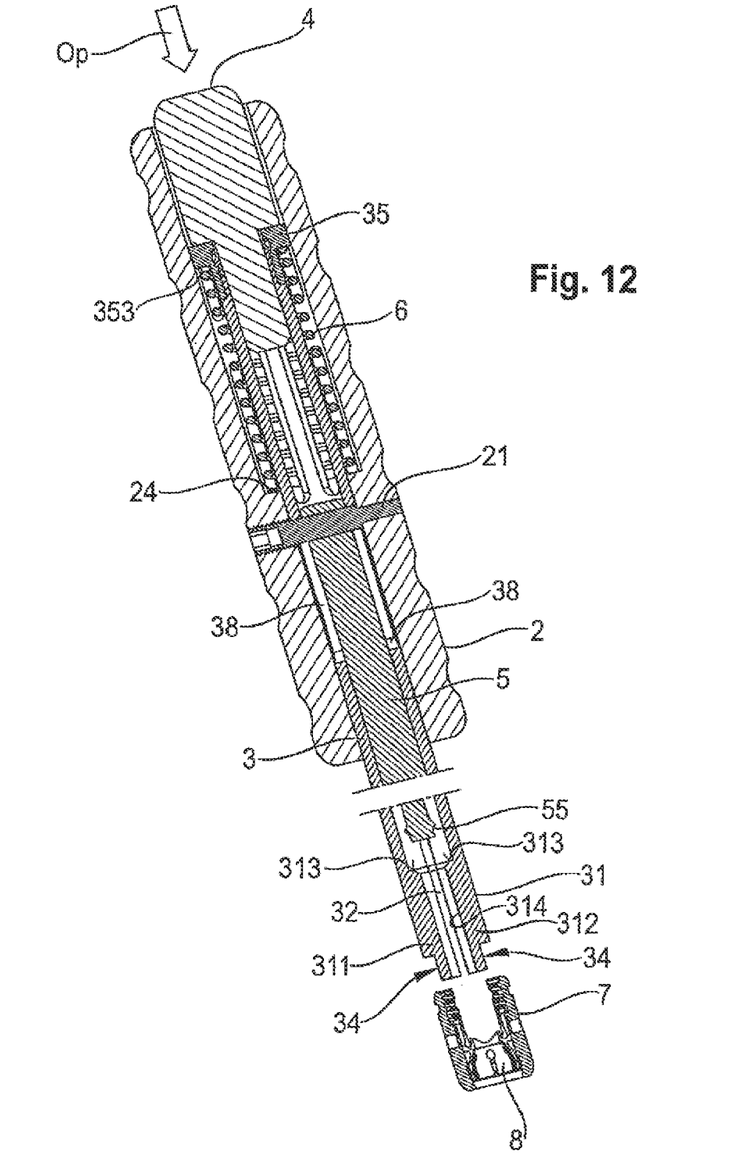
FIG. 12 shows a cross-sectional view of a first step of a method of using the device or tool shown in FIGS. 1 to 3.

As explained above, the holding portion 2 and the plunger 5 form a common unit in this embodiment where the parts are fixed relative to one another. On the other hand, the collet 3 is allowed to move with respect to those parts of the device along the longitudinal axis Z. The extent of such movement is defined by the length of the oblong hole 38 through which the fixation device 21 extends as a follower pin in an assembled state. FIGS. 12 and 14 show two different states of the device 1 in cross-sectional illustrations. More specifically, FIG. 12 shows a state in which the operation portion 4 and the collet 3 are moved distally relative to holding portion 2 and plunger 5, which yields a state in which the tip portion 52 and the conical tip portion 55 of the plunger 5 are retracted from the narrow diameter hole 314 and the shoulders 313. In this state, the tongues 311, 312 can be compressed or expanded, thereby representing an unlocked position or a release position of the device 1. In this unlocked or release position, the fixation device 21 is at a proximal end of the oblong hole 38 of the collet 3. The unlocked or release position allows easy attachment or removal of the tongues 311, 312 to the receiving part 7.

Meanwhile, FIG. 14 shows a second state in which the collet 3 has been retracted in a proximal direction relative to the holding portion 2 and the plunger 5. In this state, the tip portion 52 enters the narrow diameter bore 314 of the collet 3, thereby preventing compression of the tongues 311, 312. This state corresponds to a lock position of the plunger 5 with respect to the collet 3. The lock position may be advantageously achieved, for example, when the projections or engagement features 34 are engaged into respective features provided at the receiving part 7. Hence, a safe and secure engagement of the receiving part 7 to the device or tool 1 can be achieved. As can be seen in FIG. 14, in the lock position, the fixation device 21 is positioned at an opposite distal end of oblong hole 38. The oblong hole 38 limits the movement of the collet 3 with respect to the plunger 5, and the ends of the oblong hole 38 toward the proximal direction and distal direction define, for example, the release position and the lock position, respectively.

Returning to the description of the collet 3, the proximal end portion 35 may be formed as a separate cap-like member, as shown in FIGS. 6A through 6C. The proximal end portion 35 includes a cylindrical tubular portion 352 having an inner thread 351 that can be threaded on an outer thread 36 provided at a proximal end of the tubular portion of the collet 3 as shown in FIG. 5B. The proximal end portion 35 further has an inner bore 354 sized to receive therein a pin-like projection 42 of the operation portion 4 shown in FIG. 9. The cylindrical portion 352 has the same outer diameter as that of the cylindrical tube portion 37 of the collet 3. Further, a cap-like annular projection 355 is provided on the proximal end portion 35 whose diameter corresponds to that of the first bore portion 22 of the holding portion 2. As a consequence, a surface at a bottom side of the annular projection 355 serves as an abutment face 353 for a proximal end of the resilient member 6.

As can be seen from FIGS. 12 and 14, the resilient member 6 is held within the first bore portion 22 of the holding portion 2 and urges the proximal end portion 35 of the collet 3 away from the abutment face 24 of the holding portion 2 in a proximal direction. Thus, in a state where no external forces are exerted onto the operation portion 4, as shown in FIG. 14, the operation portion 4 and the collet 3, together with its proximal end portion 35, are retracted in the proximal direction relative to the holding portion 2 and the plunger 5.

Next, an embodiment of a receiving part 7 of the bone anchoring device that is suitable for interaction with the device or tool 1 is described with reference to FIGS. 10A and 10B. The receiving part 7 has a bore 700 extending from a first end 72 (e.g., a top end) towards a second end 73 (e.g., a bottom end), wherein an opening 701 is formed at the bottom end 73. Adjacent to the opening 701, a seat 75 is formed which defines an accommodation space for accommodating a head receiving portion 82 of an inner cap 8, which in turn is configured to clamp a head 91 of a bone anchoring element 9 such as that shown in FIG. 2. The bore 700 includes an inner wall 71 and, at an upper portion of the inner wall 71, an inner thread is formed for receiving a locking device (not shown), such as a setscrew. An abutment feature 76, such as a recess, is formed in a middle portion of the inner wall 71 and is configured to receive corresponding abutment features 813, 814 (e.g., projections) of the inner cap 8 shown in FIGS. 11A and 11B.

The receiving part 7 also includes a rod receiving channel 74 which extends from the first end 72 and has a substantially U-shape. The rod receiving channel 74 thus forms two legs and two inner walls 79 having the U-shape. As can be seen particularly in FIG. 10B, two recesses or engagement features 77 having rounded edges are formed in an upper portion of each of the inner walls 79. These engagement features 77 are configured and shaped to receive the engagement features 34 provided at the distal end portion 31 of the collet 3 of the device 1. The recesses 77 each extend in a lateral direction, perpendicular to a longitudinal axis of the bore 700, which will also be coaxial with the longitudinal axis Z of the collet 3 when the receiving part 7 is assembled with the device or tool 1. Accordingly, the lateral or radial expansion and compression of the distal end portion 31 (e.g., of the tongues 311, 312), respectively, facilitates engagement and disengagement of the receiving part 7 with the device 1.

Figure 10A:
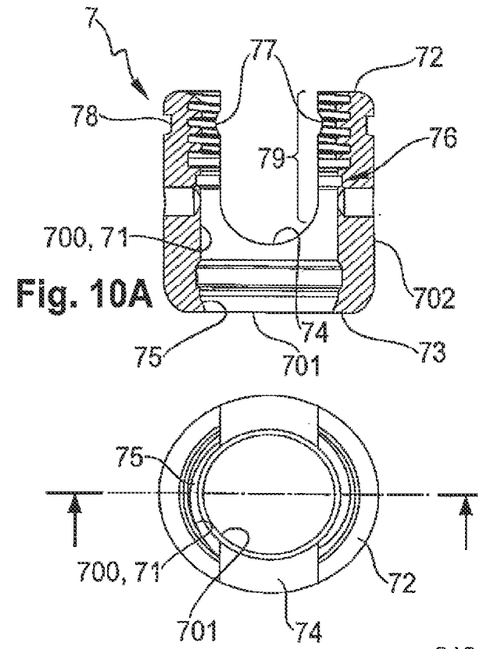
FIG. 10A shows top and cross-sectional views of a receiving part of a bone anchoring device according to an embodiment of the invention.
Figure 10B:
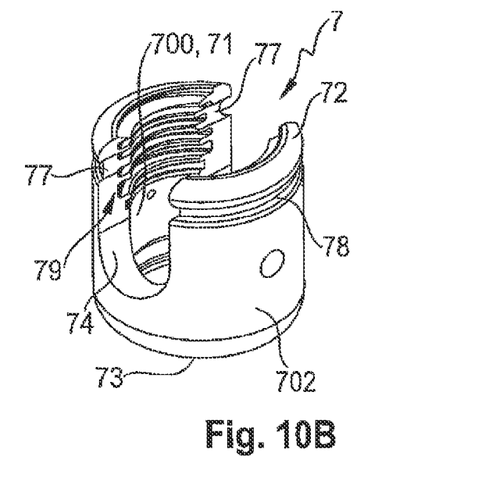
FIG. 10B shows a perspective view of the receiving part shown in FIG. 10A.

It may be noted that the receiving part 7 shown in FIGS. 10A and 10B further includes another engagement feature 78 provided at a circumferential surface 702 of the receiving part 7. The engagement feature 78 can allow for engaging of the receiving part 7 externally with other instruments as known in the art.

Figure 11A:
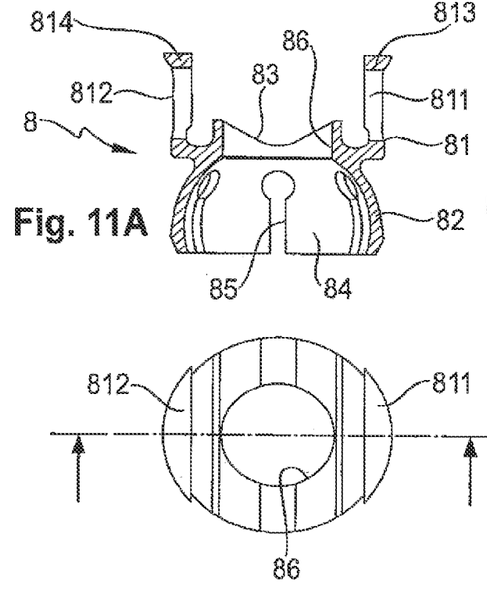
FIG. 11A shows top and cross-sectional views of an inner cap of the bone anchoring device according to an embodiment of the invention.
Figure 11B:
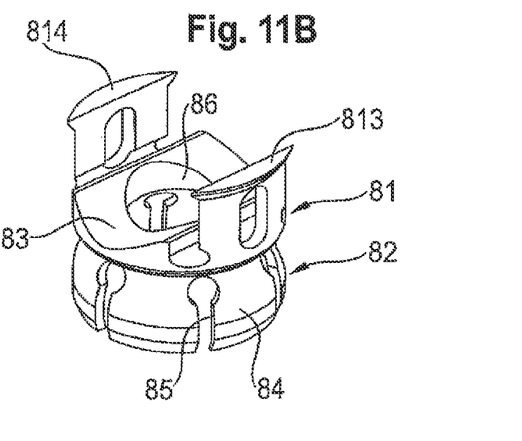
FIG. 11B shows a perspective view of the inner cap shown in FIG. 11A.

An example of an inner cap 8 for use with the receiving part 7 in one embodiment of the bone anchoring device is illustrated in FIGS. 11A and 11B. The inner cap 8 includes a substantially cylindrical portion 81 and a substantially semi-spherical head receiving portion 82. The head receiving portion 82 has resilient flanges 84 separated by slots 85, where the flanges 84 are together configured to receive and clamp the head 91 of the bone anchoring element 9 in a snap-on fashion. In the clamped state, a resilient force can be exerted onto the head 91, to provide some friction against free pivoting movement of the bone anchoring element 9. Such a feature provides an advantageous degree of pre-locking for the bone anchoring device.

The cylindrical portion 81 has a diameter substantially corresponding to the diameter of the bore 700 and, as explained above, the abutment features 813, 814 provided at tips of legs 811, 812 may abut against edges of the recess 76 to prevent the inner cap 8 from falling out of the bore 700. Moreover, the recess 76 is provided at a distance from the opening 701 of the receiving part 7 such that, upon introduction of the head 91 through the opening 701, the inner cap 8 may move upward allowing the flanges 84 to expand and to snap on the head 91. Upon final locking of the head 91, the inner cap 8 is urged down toward the seat 75 to compress the flanges 84 onto the spherical head 91 of the bone anchoring element 9.

Figure 13A:
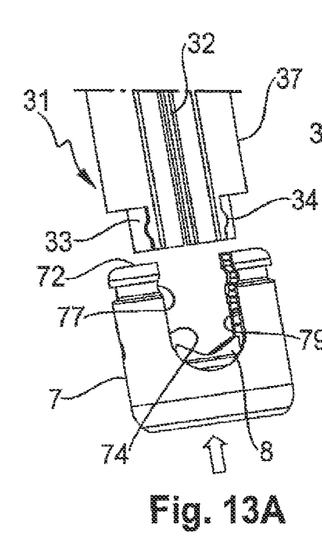
FIG. 13A shows an enlarged perspective view of the distal end portion of the collet of the device or tool and the receiving part in the same state shown in FIG. 12.
Figure 13B:
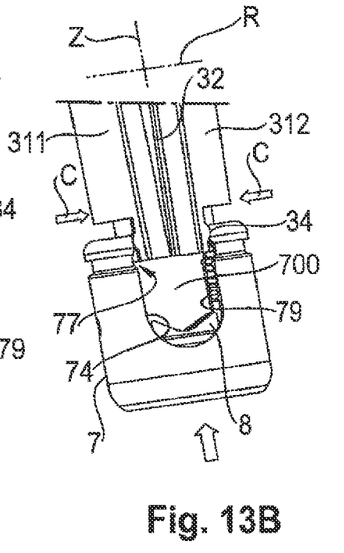
FIG. 13B shows a second step of advancing the distal end portion of the collet into the receiving part.
Figure 13C:
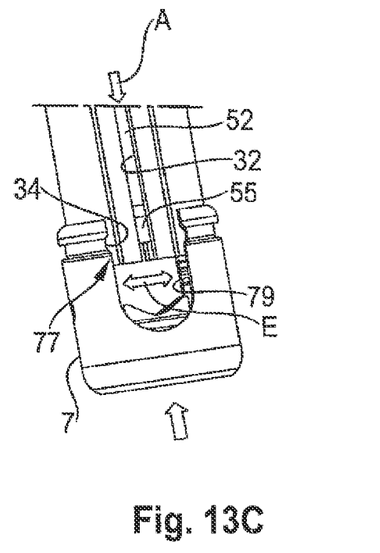
FIG. 13C shows a third step in which the distal end portion of the collet is engaged with inner walls of the receiving part.

Next, operation of the device or tool 1 with the receiving part 7, or a method of use, is explained with reference to FIGS. 12 through 16C. FIGS. 12 through 14 illustrate steps of engaging the receiving part 7 with the device 1, while FIGS. 15A through 16C reveal steps of placing and releasing the receiving part 7 on and from the head 91 of the bone anchoring element 9, respectively.

FIGS. 12 and 13A show a first step of the process, before engagement of the device or tool 1 with the receiving part 7. As can be seen in FIG. 12, the operation portion 4 is already actuated (arrow Op) against the urging force of the coil spring of resilient member 6. Consequently, the operation portion 4 and the collet 3 with the proximal end portion 35 are advanced distally relative to the holding portion 2 and the plunger 5, or put another way, the holding portion 2 and the plunger 5 are retracted proximally relative to the collet 3. As a result, the tip portion 52 including the conical tip portion 55 of the plunger 5 is retracted from the narrow diameter hole 314 inside the distal end portion 31 of the collet 3. The tongues 311, 312 can then be resiliently compressed.

A second step of the process is shown in FIG. 13B. The tip portion 33 of the distal end portion 31 is introduced into an inner space of the receiving part 7 formed by the bore 700 and the rod receiving channel 74. The distal end portion 31 is introduced into the receiving part 7 along the longitudinal axis Z of the collet 3. Because the cross-sectional profile of the tip portion 33 of the collet 3 corresponds to the cross section of the inner space of the receiving part 7, the tip portion 33 may initially fit snugly into the inner space. However, the engagement features 34 protrude laterally outward from other parts of the tip portion 33 and eventually abut the top edges of the rod receiving channel 74. Due to the rounded surfaces of the engagement features 34, the tongues 311, 312 deflect radially inward along a direction R perpendicular to the longitudinal axis Z, i.e., the tongues 311, 312 are compressed towards each other (see arrows C).

As shown in FIG. 13C, the engagement features 34 then latch into respective recesses of the engagement features 77, thereby allowing the tongues 311, 312 to expand again (see arrows E). FIG. 14 shows the same third step of the process shown in FIG. 13C, and it becomes apparent that releasing the operation portion 4 leads to a retraction of the collet 3 relative to the plunger 5 (see arrow A), or put another way, an advancement of the holding portion 2 and the plunger 5 distally relative to the collet 3, due to the urging force of the resilient member 6. Thereby, the conical tip portion 55 and the tip portion 52 of the plunger 5 enter the narrow diameter hole 314 of the collet 3, locking the engagement between the collet 3 and the receiving part 7 (i.e., in the "lock position"). More specifically, the tip portion 52 prevents any further compression of the tongues 311, 312, such that engagement features 34 cannot be easily released from engagement features 77. Moreover, further tightening or attachment of the receiving part 7 to the collet 3 is achieved by the conical tip portion 55, which expands or urges the tip portion 33 and the engagement features 34 further into the engagement features 77 of the receiving part 7.

In this arrangement, as shown in FIG. 14, the operation portion 4 may be removed from the device 1 as indicated by arrow Rem. Removal of the operation portion 4 prevents unintended release of the receiving part 7, for example, during intermediate steps of the method. Meanwhile, due to the structure of the device 1 and the receiving part 7, release of the receiving part 7 from the collet 3 after placement or implantation of the receiving part 7 can be accomplished via a simple withdrawal movement of the device 1, as will be further explained below.

Figures 15A, 15B:
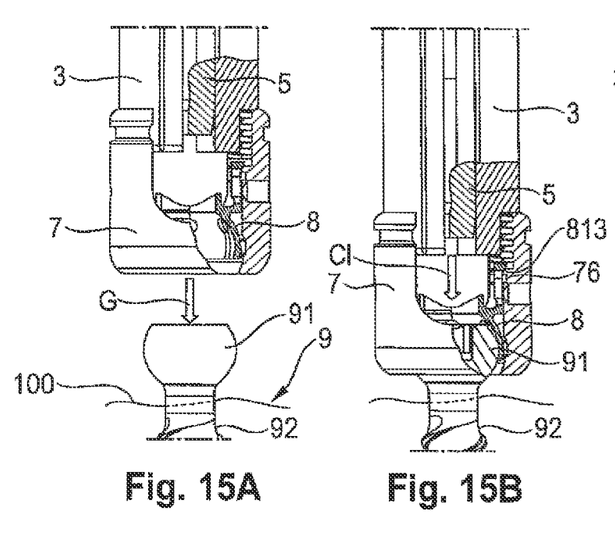
FIG. 15A shows a partial cross-sectional view of a fourth step of the method of using the device in which the device and receiving part are guided to a head of a bone anchoring element when in the state shown in FIG. 14.
FIG. 15B shows a fifth step in which the head is introduced and snapped into an inner cap in the receiving part.

FIG. 15A shows a fourth step of the method. The receiving part 7 is guided by the device 1 through an incision (not shown) in the tissue of the patient towards the head 91 of the bone anchoring element 9, whose shank 92 has already been driven into bone material of a vertebra 100 (see arrow G).

FIG. 15B shows a fifth step of the method in which the head 91 is introduced through the bottom opening 701 into the accommodation space of the bore 700 and clicked into the head receiving portion 82 of the inner cap 8 (see arrow Cl). Thereby, prior to being clicked into the head receiving portion 82 and clamped in a pre-lock position, the inner cap 8 first moves upwards within the bore 700 until the projections 813 latch into the recesses 76 and abut against upper edges or surfaces of the recesses 76. This abutment prevents the inner cap 8 from moving further upwards. Having reached this position, the flanges 84 of the head receiving portion 82 can be deflected outwards to receive the head 91 therein in a snap-on fashion.

Figure 15C:
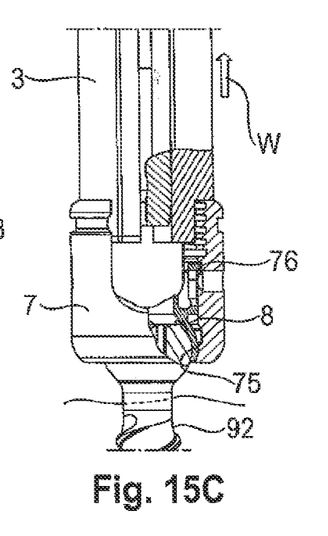
FIG. 15C shows a sixth step in which the device is drawn or pulled in a direction away from the receiving part.

As shown in FIG. 15C, the device or too 1 can then be pulled in a proximal direction away from the bone anchoring element 9 (see arrow W), and as a result, the inner cap 8 moves downward within the bore 700 (e.g., the receiving part moves up as illustrated) and is pressed against the seat 75 by the pulling force. As a consequence, the head 91 is clamped within the inner cap 8 and the receiving part 7 cannot move further up easily and also cannot be easily released from the clamped state.

Figure 16A:
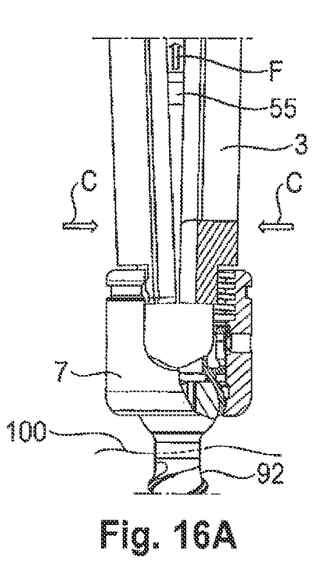
FIG. 16A shows a seventh step in which the distal end portion of the device or tool is unlocked.
Figure 16B:
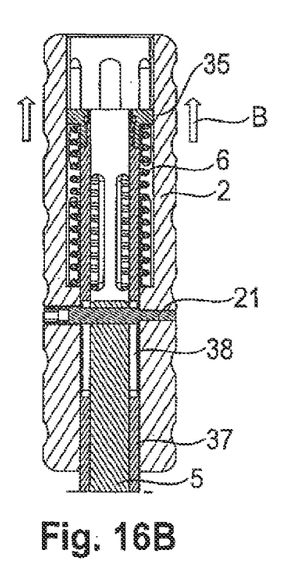
FIG. 16B is a cross-sectional view showing a proximal portion of the device or tool with the tensioned resilient member.

FIGS. 16A and 16B show a seventh step of the method in which, as shown in FIG. 16B, further proximal pulling of the holding portion 2 leads to compression of the resilient member 6 because the holding portion 2 is effectively drawn upwards or proximally by the operating staff, while the collet 3 remains stationary relative to the receiving part 7. Once the head 91 and the inner cap 8 are in the clamped state shown in FIG. 15C, the collet 3 cannot be drawn further up easily, and the holding portion 2 can then be moved with respect to collet 3 under the increasing upward tensioning or biasing force exerted on the coil spring of the resilient member 6 when the holding portion 2 is still being pulled up (see arrow B). This, in turn, leads to retraction (see arrow F) of the plunger 5 and the conical tip portion 55 from the distal end portion 31 of collet 3. Upon such tensioning, the position of the plunger 5 corresponds to the released or unlocked position with respect to the distal end portion 31, and further withdrawing of the device 1 in the proximal direction allows compression of the tongues 311, 312 (see arrow C in FIG. 16A) and, therefore, release of the device or tool 1 from attachment with the receiving part 7. As noted above, upon drawing up the holding portion 2, the resilient member 6 is tensioned with an increasing force. Thereby, the resilient member 6 is configured or selected to be tensioned or compressed by an amount of force that is less than a clamping force exerted by the flexible head receiving portion 82 of the inner cap 8 on the head 91. Hence, the receiving part 7 is released by the device or tool 1 before the head 91 can unclamp or be removed from the inner cap 8, even when the head receiving portion 82 is not pressed against the seat 75.

Figure 16C:
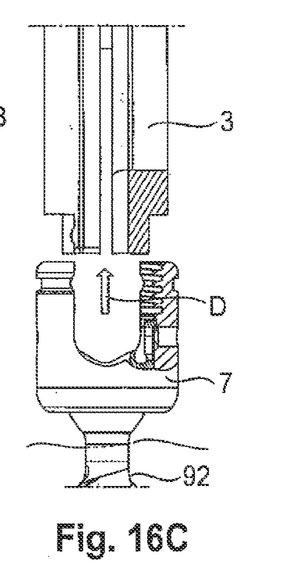
FIG. 16C shows a subsequent step of the method of using the device or tool in which the unlocked distal end portion of the collet of the device is released from the receiving part.

As shown in FIG. 16C, the collet 3 can then disengage from the receiving part 7 (see arrow D) which has now been safely placed onto the head 91 of the bone anchoring element 9. Meanwhile, since forces are no longer exerted onto the device 1 by the receiving part 7, the collet 3 is then immediately retracted proximally relative to the holding portion 2, again, under the urging force of the resilient member 6, such that the device 1 returns into its initial locked state.

Meanwhile, the released receiving part 7 is pre-locked, which means that, by virtue of friction created between the head receiving portion 82 and the clamped head 91, the receiving part 7 assumes and is held at a certain posture or angular position with respect to the bone anchoring element 9, which can still be easily repositioned by hand or by an instrument. Further possible steps include supplying a spinal rod (not shown) to the receiving part 7, wherein the spinal rod is inserted into the rod receiving channel 74. Moreover, a locking screw (not shown) can then be screwed into the inner thread at the inner wall 79 of the receiving part 7 to lock the spinal rod in the receiving part 7, where the spinal rod can then press onto a U-shaped or V-shaped groove at the cylindrical portion 81 of the inner cap 8, to push or urge the inner cap 8 further downwards in the receiving part 7 in order to firmly and finally lock the receiving part 7 and head 91 together.

It may be noted that various modifications may be applied to the various aspects and embodiments of the invention which are within the scope of the appended claims and their equivalents. For example, in the above embodiments, metal materials, such as titanium, nickel titanium alloys, Nitinol, or other body-compatible metals, can be employed for each of the components. However other materials, such as plastic materials, PEEK, etc., can also be used.

Moreover, in the above embodiments, a receiving part employing an inner cap having a specific head clamping function is used. Nevertheless, other structures of receiving parts having, for example, pressure elements and/or other inner caps may also be used.

Meanwhile, in the above embodiments, tongues on the device or tool are expanded to engage engagement features provided at a receiving part. However, other engagement features may also be used. For example, it is also contemplated that movable engagement parts may be provided at a tip of a shaft which expand within an inner space of a receiving part upon engagement.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A bone anchoring device for connecting a bone anchoring element having a head and a shank to a spinal rod, the bone anchoring device comprising:
    a locking element; and
    a receiving part having a top end, a bottom end, and a longitudinal axis extending between the top and bottom ends, and comprising:
        an outer wall extending from the top end to the bottom end; and
        an inner wall facing radially inwardly towards the longitudinal axis and defining a bore extending from the top end towards the bottom end, an accommodation space for accommodating the head of the bone anchoring element, and an opening at the bottom end that opens into the accommodation space;
    wherein a rod receiving channel with a U-shaped profile has a first portion that extends transversely through a first side of the receiving part to form opposing sidewalls that face one another and that extend continuously from the outer wall to the inner wall on one side of the bore, and a second portion that extends transversely through an opposite second side of the receiving part;
    wherein the locking element is engageable with an engagement surface to block removal of the spinal rod from the top end of the receiving part, the engagement surface being formed on the inner wall and extending at least partially into the opposing sidewalls; and
    wherein a downward facing surface directed at least partially towards the bottom end of the receiving part is formed in at least one of the opposing sidewalls and extends continuously from the outer wall to the inner wall for engaging a corresponding upward facing surface of a device configured to place the receiving part onto the head of the bone anchoring element, and wherein at least part of the downward facing surface is at a same axial height on the receiving part as part of the engagement surface.

2. The bone anchoring device of claim 1, wherein the downward facing surface extends from the outer wall of the receiving part to the inner wall of the receiving part along an axis that is parallel with an axis of the rod receiving channel.

3. The bone anchoring device of claim 2, wherein the downward facing surface is a first downward facing surface, wherein the second portion of the rod receiving channel forms another pair of opposing sidewalls that face one another on an opposite second side of the bore, and wherein a second downward facing surface is formed in at least one of the another pair of opposing sidewalls and extends along an axis that is coaxial with the axis of the first downward facing surface.

4. The bone anchoring device of claim 1, wherein the downward facing surface is a first downward facing surface, and wherein a second downward facing surface is formed in the other one of the opposing sidewalls at a same axial height on the receiving part as the first downward facing surface.

5. The bone anchoring device of claim 1, wherein the downward facing surface is formed by a recess in the receiving part.

6. The bone anchoring device of claim 1, wherein at least part of the downward facing surface is at a same axial height on the receiving part as part of the engagement surface for the locking element.

7. The bone anchoring device of claim 6, wherein the engagement surface for the locking element comprises a thread, and wherein the at least part of the downward facing surface is at a same axial height as part of the thread.

8. The bone anchoring device of claim 1, further comprising an inner cap comprising a flexible head receiving portion configured to resiliently clamp the head of the bone anchoring element, the inner cap being movable in the accommodation space.

9. The bone anchoring device of claim 1, further comprising the bone anchoring element having the head and the shank.

10. The bone anchoring device of claim 9, wherein the head of the bone anchoring element is insertable through the opening into the accommodation space of the receiving part.

11. A device configured to place a receiving part onto a head of a bone anchoring element, the receiving part comprising a top end, a bottom end, a longitudinal axis extending between the top and bottom ends, an outer wall extending from the top end to the bottom end, and an inner wall facing radially inwardly towards the longitudinal axis and defining a bore extending from the top end towards the bottom end, an accommodation space for accommodating the head of the bone anchoring element, and an opening at the bottom end that opens into the accommodation space, wherein a rod receiving channel with a U-shaped profile has a first portion that extends transversely through a first side of the receiving part to form opposing sidewalls that face one another and that extend continuously from the outer wall to the inner wall on one side of the bore, and a second portion that extends transversely through an opposite second side of the receiving part, the device comprising:

a radially outwardly facing portion insertable from the top end of the receiving part into the bore;

a laterally extending portion that extends laterally away from the radially outwardly facing portion and that is configured to extend into the rod receiving channel of the receiving part when the radially outwardly facing portion is in the bore; and     at least one projection that extends circumferentially from an outer surface of the laterally extending portion to engage a corresponding recess formed in at least one of the opposing sidewalls of the receiving part to connect the device to the receiving part for placing the receiving part onto the head of the bone anchoring element.

12. The device of claim 11, wherein an axially extending slot separates a distal end of the device into two axially extending sections that are radially flexible.

13. The device of claim 12, wherein the slot separates both the radially outwardly facing portion and the laterally extending portion into respective halves.

14. The device of claim 12, further comprising a plunger positionable between at least part of the two axially extending sections and movable axially relative to the two axially extending sections to selectively prevent or allow the two axially extending sections to move radially towards one another for respectively connecting and disconnecting the receiving part and the device from one another.

15. The device of claim 11, wherein the radially outwardly facing portion comprises at least one cylindrical segment-shaped region.

16. The device of claim 15, wherein the laterally extending portion extends radially outwardly from the cylindrical segment-shaped region of the radially outwardly facing portion.

17. A method of using a device to place a receiving part onto a head of a bone anchoring element to connect the bone anchoring element to a spinal rod, the receiving part comprising a top end, a bottom end, a longitudinal axis extending between the top and bottom ends, an outer wall extending from the top end to the bottom end, an inner wall facing radially inwardly towards the longitudinal axis and defining a bore extending from the top end towards the bottom end, an accommodation space for accommodating the head of the bone anchoring element, and an opening at the bottom end that opens into the accommodation space, and a rod receiving channel having a U-shaped profile that extends transversely through the receiving part for receiving the rod, the device comprising a central portion and a non-threaded engagement surface that extends away from the central portion, the method comprising:

inserting the central portion of the device from the top end of the receiving part into the bore;

engaging the non-threaded engagement surface of the device with a portion of the receiving part that is away from the outer wall, wherein the non-threaded engagement surface is directed at least partially towards the top end of the receiving part when engaged to restrict detachment of the receiving part from the device;

advancing the device with the connected receiving part towards a bone anchoring element that is already anchored in bone;

inserting the head of the bone anchoring element through the opening of the receiving part and into the accommodation space to attach the receiving part to the head while the receiving part is connected to the device; and     disengaging the non-threaded engagement surface of the device from the receiving part to release the connection between the receiving part and the device.

18. The method of claim 17, wherein the device is adjustable from a first configuration where the non-threaded engagement surface is radially compressible to facilitate insertion of the central portion into the bore, to a second configuration where the non-threaded engagement surface is prevented from radially compressing to engage the non-threaded engagement surface with the receiving part.

19. The method of claim 17, wherein the receiving part further comprises an inner cap movable in the accommodation space to clamp the head of the bone anchoring element therein.

20. The method of claim 17, wherein when the device and the receiving part are fully connected to one another, the device is devoid of any portions that extend around an outside of the receiving part.

\* \* \* \* \*